US009532749B2

(12) United States Patent
Jung et al.

(10) Patent No.: US 9,532,749 B2
(45) Date of Patent: Jan. 3, 2017

(54) REPETITIVE STRAIN MITIGATION

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US)

(73) Assignee: Invention Science Fund I, LLC, Bellevue, WA (US)

( * ) Notice: Subject to any disclaimer, the term of this patent is extended or adjusted under 35 U.S.C. 154(b) by 0 days.

(21) Appl. No.: 11/901,954

(22) Filed: Sep. 18, 2007

(65) Prior Publication Data

US 2009/0076418 A1   Mar. 19, 2009

(51) Int. Cl.
*A61B 5/00*    (2006.01)
*A61B 5/11*    (2006.01)

(52) U.S. Cl.
CPC .......... *A61B 5/7275* (2013.01); *A61B 5/11* (2013.01); *A61B 5/486* (2013.01)

(58) Field of Classification Search
CPC ....... A61B 5/11; A61B 5/1101; A61B 5/1124; A61B 5/1125; A61B 5/1126; A61B 5/1128; A61B 5/486; A61B 5/7275
USPC ......... 600/544–546, 587, 594, 595; 128/898, 128/905; 340/573.1, 573.7, 539.12; 351/239; 705/1
See application file for complete search history.

(56) References Cited

U.S. PATENT DOCUMENTS

| 6,647,288 | B2 * | 11/2003 | Madill et al. ............... 600/546 |
| 2001/0015792 | A1 * | 8/2001 | Fateh et al. ................. 351/239 |
| 2004/0210447 | A1 * | 10/2004 | Zingarelli ....................... 705/1 |
| 2005/0270163 | A1 * | 12/2005 | Littell ....................... 340/573.7 |
| 2006/0184059 | A1 * | 8/2006 | Jadidi ........................... 600/546 |
| 2012/0092157 | A1 * | 4/2012 | Tran ....................... 340/539.12 |

OTHER PUBLICATIONS

Elgan, Mike; "Will Microsoft beat Apple with its 'giant iPhone'"; Computerworld.com; May 31, 2007; pp. 1-4; printed on Sep. 11, 2007; located at http://www.computerworld.com/action/article.do?command=printArticleBasic&articleId=9022418.
Marxhausen, Paul; "Computer Related Repetitive Strain Injury"; bearing dates of 1996-2005; pp. 1-24; printed on Sep. 11, 2007; located at http://eeshop.unl.edu/rsi.html.
"Repetitive strain injury"; Wikipedia.com; bearing a date of Sep. 10, 2007; pp. 1-4; Wikimedia Foundation, Inc.; printed on Sep. 11, 2007; located at http://en.wikipedia.org/wiki/Repetitive_strain_injury.

\* cited by examiner

*Primary Examiner* — Max Hindenburg

(57) ABSTRACT

Embodiments provide an apparatus, a system, a device, a computer program product, and a method. A method embodiment includes a method implemented in an environment that includes a person interacting with an electronic device via a user interface. The method includes monitoring at least one of a movement or a position of an appendage of the person with respect to the user interface of the device. The method also includes determining if the monitored movement or position of the appendage of the person is indicative of a risk of a repetitive injury to the person. The method further includes implementing an action facilitating a reduction of the determined indicated risk of a repetitive injury to the person.

26 Claims, 11 Drawing Sheets

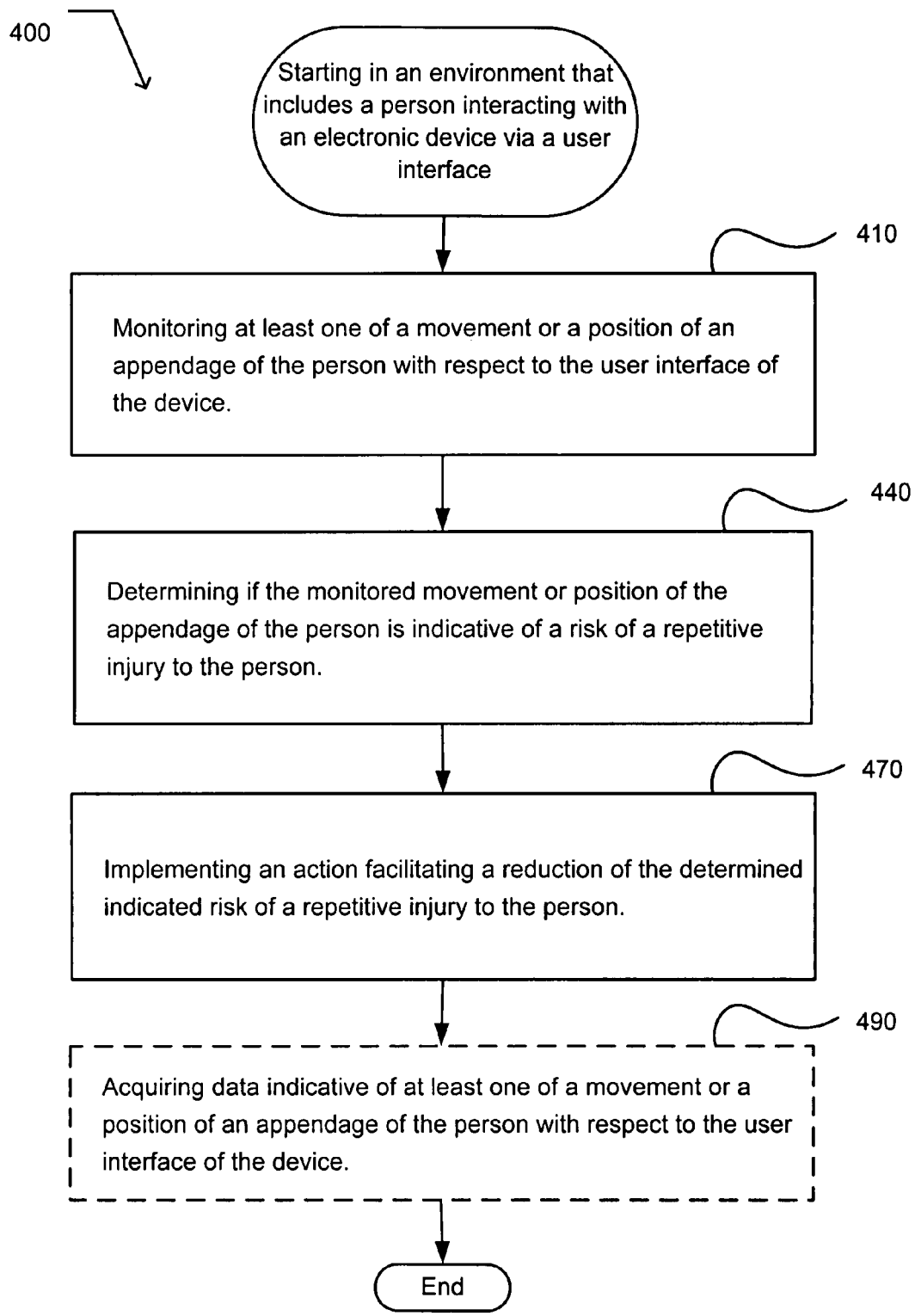

FIG. 5

410 — Monitoring at least one of a movement or a position of an appendage of the person with respect to the user interface of the device.

412 Monitoring at least one of a multi-touch movement of an appendage of the person with respect to the user interface of the device.

414 Monitoring at least one of a movement or a position of at least one of a head, arm, arms, wrist, hand, wrists, finger, fingers, finger speed, finger position with respect to keyboard, finger spreading, or finger striking force of the person with respect to the user interface of the device.

416 Monitoring for at least one of a class of risky repetitive movements or positions of the person with respect to the user interface of the device.

418 Monitoring at least one of a movement or a position of an appendage of the person with respect to a user input interface, and/or a user output interface of the device.

422 Monitoring at least one of a movement or a position of an appendage of the person with respect to at least one of a keyboard, mouse, display screen, touch display screen, touch display surface, or interactive display surface of the electronic device.

Determining if the monitored movement or position of the appendage of the person is indicative of a risk of a repetitive injury to the person.

| 442 Determining if the monitored current movement or current position of the appendage of the person is indicative of a risk of a repetitive injury to the person. | 444 Determining if a combination of the monitored current movement or current position of the appendage of the person and a monitored a past movement or a past position of the appendage of the person indicates a risk of a repetitive injury to the person. | 446 Inferring a usage pattern in response to the monitored movement or position of the appendage of the person and determining if the inferred usage pattern indicates a risk of a repetitive injury to the person. | 448 Determining if a combination of the monitored movement or position of the appendage of the person and an inputted repetitive injury profile of the person indicates a risk to the person of a current repetitive injury. |

FIG. 8

470 — Implementing an action facilitating a reduction of the determined indicated risk of a repetitive injury to the person.

472 Displaying using the electronic device a warning facilitating a reduction of the indicated risk of a repetitive injury to the person.

474 Displaying using an aspect of the electronic device a human understandable instruction facilitating a reduction of the indicated risk of a repetitive injury to the person.

476 Displaying using an aspect of the electronic device a human understandable information facilitating a reduction of the indicated risk of a repetitive injury to the person.

478 Modifying an aspect of the user interface of the device facilitating a reduction of the indicated risk to the person of a repetitive injury.

610 Computer-readable signal-bearing medium bearing the program instructions.

620 Program instructions operable to perform a process in a computing device having a user interface operable to interact with a person, the process comprising:

monitoring at least one of a movement or a position of an appendage of the person with respect to the user interface of the device;

determining if the monitored movement or position of the appendage of the person is indicative of a risk of a repetitive injury to the person; and implementing an action facilitating a reduction of the determined indicated risk of a repetitive injury to the person.

612 Computer storage medium.

614 Communication medium.

FIG. 11

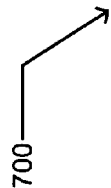

705 Electronic device having a user interface operable to interact with a person.

710 Means for monitoring at least one of a movement or a position of an appendage of the person with respect to the user interface of the device.

720 Means for determining if the monitored movement or position of the appendage of the person is indicative of a risk of a repetitive injury to the person.

730 Means for implementing an action facilitating a reduction of the determined indicated risk of a repetitive injury to the person.

REPETITIVE STRAIN MITIGATION

SUMMARY

An embodiment provides method implemented in an environment that includes a person interacting with an electronic device via a user interface. The method includes monitoring at least one of a movement or a position of an appendage of the person with respect to the user interface of the device. The method also includes determining if the monitored movement or position of the appendage of the person is indicative of a risk of a repetitive injury to the person. The method further includes implementing an action facilitating a reduction of the determined indicated risk of a repetitive injury to the person. In an embodiment, the method may further include acquiring data indicative of at least one of a movement or a position of an appendage of the person with respect to the user interface of the device. In addition to the foregoing, other method embodiments are described in the claims, drawings, and text that form a part of the present application.

Another embodiment provides an electronic device. The electronic device includes a user interface operable to at least one of receive input from a person or provide an output to the person. The electronic device also includes a monitoring circuit operable to gather data indicative of a physical movement involved in the person making an input to the electronic device using the user interface. The electronic device further includes an analytic circuit operable to determine if the movement of the person making an input to the electronic device corresponds to a repetitive injury risk to the person. The electronic device also includes a mitigation circuit operable to implement a remediation action facilitating a reduction of the determined repetitive injury risk to the person. In an alternative embodiment, the electronic device may further include a selector circuit operable to pick the risk remediation action usable in facilitating a reduction of the determined repetitive injury risk to the person. In addition to the foregoing, other device embodiments are described in the claims, drawings, and text that form a part of the present application.

A further embodiment provides a computer program product. The computer program product includes a computer-readable signal-bearing medium bearing program instructions. The program instructions include program instructions operable to perform a process in a computing device having a user interface operable to interact with a person. The process includes monitoring at least one of a movement or a position of an appendage of the person with respect to the user interface of the device. The process also includes determining if the monitored movement or position of the appendage of the person is indicative of a risk of a repetitive injury to the person. The process further includes implementing an action facilitating a reduction of the determined indicated risk of a repetitive injury to the person. In addition to the foregoing, other computer program product embodiments are described in the claims, drawings, and text that form a part of the present application.

An embodiment provides an electronic device having a user interface operable to interact with a person. The electronic device includes means for monitoring at least one of a movement or a position of an appendage of the person with respect to the user interface of the device. The electronic device also includes means for determining if the monitored movement or position of the appendage of the person is indicative of a risk of a repetitive injury to the person. The electronic device also includes means for implementing an action facilitating a reduction of the determined indicated risk of a repetitive injury to the person. In addition to the foregoing, other device embodiments are described in the claims, drawings, and text that form a part of the present application.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 4 illustrates an example of an operational flow implemented in an environment that includes a person interacting with an electronic device via a user interface;

FIG. 5 illustrates an alternative embodiment of the operational flow of FIG. 4;

FIG. 7 illustrates a further alternative embodiment of the operational flow of FIG. 4;

FIG. 8 illustrates an alternative embodiment of the operational flow of FIG. 4;

FIG. 10 illustrates an example computer program product; and

FIG. 11 illustrates an example system.

DETAILED DESCRIPTION

Figure 1:
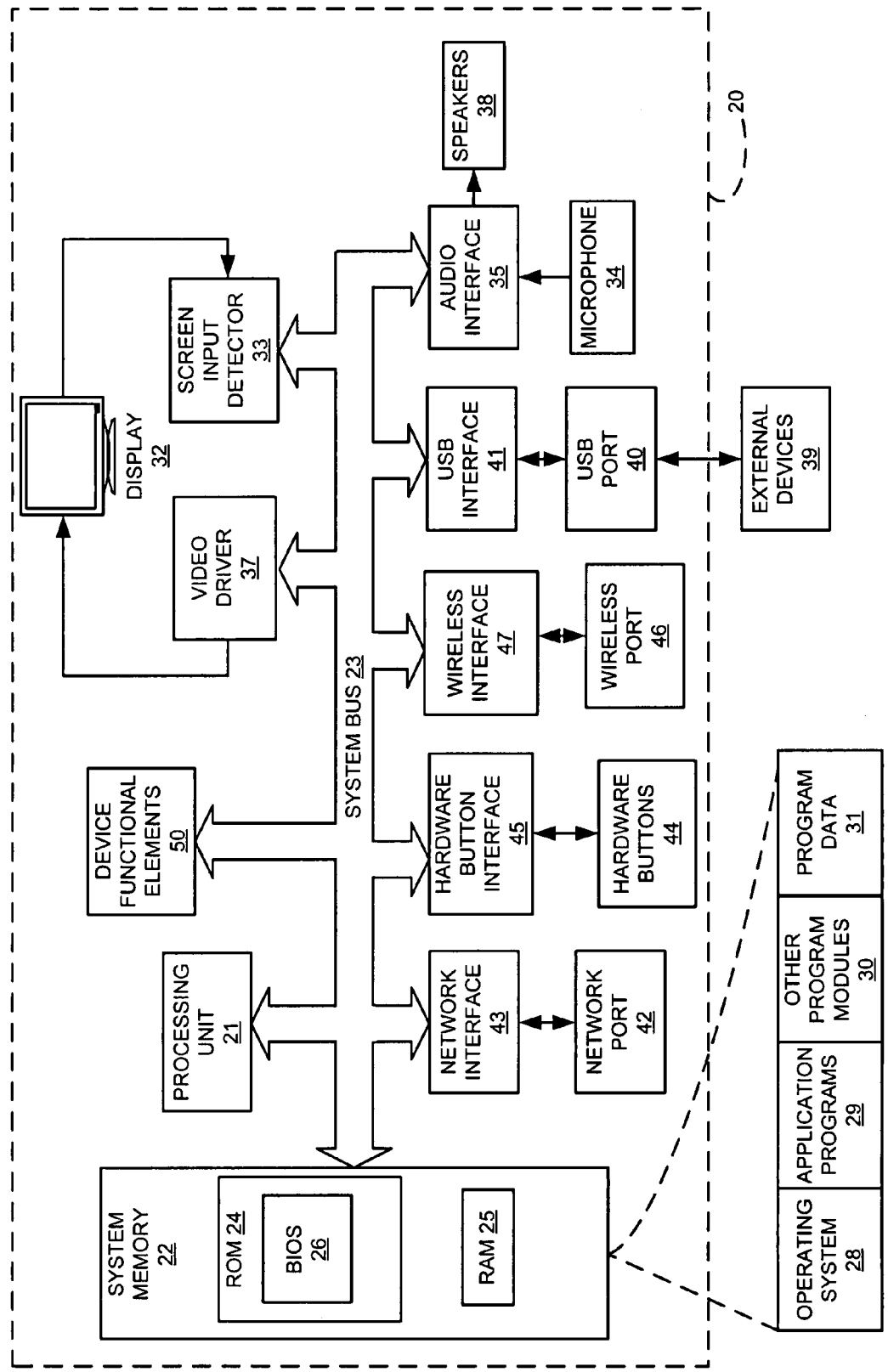
FIG. 1 illustrates an exemplary embodiment of a thin computing device in which embodiments may be implemented.

In the following detailed description, reference is made to the accompanying drawings, which form a part hereof. In the drawings, similar symbols typically identify similar components, unless context dictates otherwise. The illustrated embodiments described in the detailed description, drawings, and claims are not meant to be limiting. Other embodiments may be utilized, and other changes may be made, without departing from the spirit or scope of the subject matter presented here.

FIG. 1 and the following discussion are intended to provide a brief, general description of an environment in which embodiments may be implemented. FIG. 1 illustrates an exemplary system that includes a thin computing device 20, which may be included in an electronic device that also includes a device functional element 50. For example, the electronic device may include any item having electrical and/or electronic components playing a role in a functionality of the item, such as a limited resource computing device, a wireless communication device, a mobile wireless communication device, an electronic pen, a handheld electronic writing device, a digital camera, a scanner, an ultrasound device, an x-ray machine, a non-invasive imaging device, a cell phone, a printer, a refrigerator, a car, and an airplane. The thin computing device 20 includes a processing unit 21, a system memory 22, and a system bus 23 that couples various system components including the system memory 22 to the processing unit 21. The system bus 23 may be any of several types of bus structures including a memory bus or memory controller, a peripheral bus, and a local bus using any of a variety of bus architectures. The system memory includes read-only memory (ROM) 24 and random access memory (RAM) 25. A basic input/output system (BIOS) 26, containing the basic routines that help to transfer information between sub-components within the thin computing device 20, such as during start-up, is stored in the ROM 24. A number of program modules may be stored in the ROM 24 and/or RAM 25, including an operating system 28, one or more application programs 29, other program modules 30 and program data 31.

A user may enter commands and information into the computing device 20 through input devices, such as a number of switches and buttons, illustrated as hardware buttons 44, connected to the system via a suitable interface 45. Input devices may further include a touch-sensitive display screen 32 with suitable input detection circuitry 33. The output circuitry of the touch-sensitive display 32 is connected to the system bus 23 via a video driver 37. Other input devices may include a microphone 34 connected through a suitable audio interface 35, and a physical hardware keyboard (not shown). In addition to the display 32, the computing device 20 may include other peripheral output devices, such as at least one speaker 38.

Other external input or output devices 39, such as a joystick, game pad, satellite dish, scanner or the like may be connected to the processing unit 21 through a USB port 40 and USB port interface 41, to the system bus 23. Alternatively, the other external input and output devices 39 may be connected by other interfaces, such as a parallel port, game port or other port. The computing device 20 may further include or be capable of connecting to a flash card memory (not shown) through an appropriate connection port (not shown). The computing device 20 may further include or be capable of connecting with a network through a network port 42 and network interface 43, and through wireless port 46 and corresponding wireless interface 47 may be provided to facilitate communication with other peripheral devices, including other computers, printers, and so on (not shown). It will be appreciated that the various components and connections shown are exemplary and other components and means of establishing communications links may be used.

The computing device 20 may be primarily designed to include a user interface. The user interface may include a character, a key-based, and/or another user data input via the touch sensitive display 32. The user interface may include using a stylus (not shown). Moreover, the user interface is not limited to an actual touch-sensitive panel arranged for directly receiving input, but may alternatively or in addition respond to another input device such as the microphone 34. For example, spoken words may be received at the microphone 34 and recognized. Alternatively, the computing device 20 may be designed to include a user interface having a physical keyboard (not shown).

The device functional elements 50 are typically application specific and related to a function of the electronic device, and is coupled with the system bus 23 through an interface (not shown). The functional elements may typically perform a single well-defined task with little or no user configuration or setup, such as a refrigerator keeping food cold, a cell phone connecting with an appropriate tower and transceiving voice or data information, and a camera capturing and saving an image.

Figure 2:
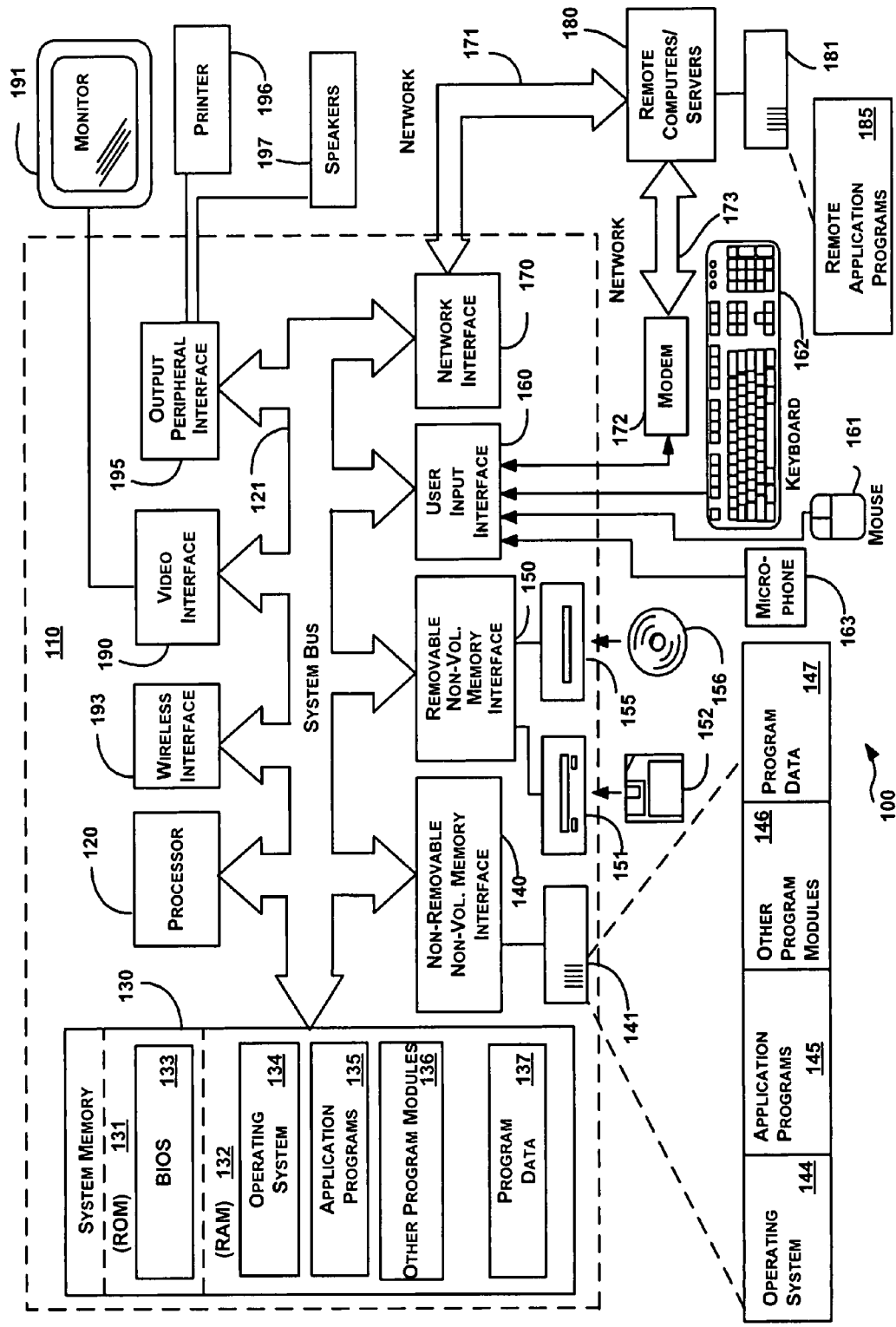
FIG. 2 illustrates an exemplary embodiment of a general-purpose computing system in which embodiments may be implemented.

FIG. 2 illustrates an exemplary embodiment of a general-purpose computing system in which embodiments may be implemented, shown as a computing system environment 100. Components of the computing system environment 100 may include, but are not limited to, a computing device 110 having a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing system environment 100 typically includes a variety of computer-readable media products. Computer-readable media may include any media that can be accessed by the computing device 110 and include both volatile and nonvolatile media, removable and non-removable media. By way of example, and not of limitation, computer-readable media may include computer storage media and communications media. Computer storage media includes volatile and nonvolatile, removable and non-removable media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 110. In a further embodiment, a computer storage media may include a group of computer storage media devices. In another embodiment, a computer storage media may include an information store. In another embodiment, an information store may include a quantum memory, a photonic quantum memory, and/or atomic quantum memory. Combinations of any of the above may also be included within the scope of computer-readable media.

Communications media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communications media include wired media such as a wired network and a direct-wired connection and wireless media such as acoustic, RF, optical, and infrared media.

The system memory 130 includes computer storage media in the form of volatile and nonvolatile memory such as ROM 131 and RAM 132. A RAM may include at least one of a DRAM, an EDO DRAM, a SDRAM, a RDRAM, a VRAM, and/or a DDR DRAM. A basic input/output system (BIOS) 133, containing the basic routines that help to transfer information between elements within the computing device 110, such as during start-up, is typically stored in ROM 131. RAM 132 typically contains data and program modules that are immediately accessible to or presently being operated on by processing unit 120. By way of example, and not limitation, FIG. 2 illustrates an operating system 134, application programs 135, other program modules 136, and program data 137. Often, the operating system 134 offers services to applications programs 135 by way of one or more application programming interfaces (APIs) (not shown). Because the operating system 134 incorporates these services, developers of applications programs 135 need not redevelop code to use the services. Examples of APIs provided by operating systems such as Microsoft's "WINDOWS" are well known in the art.

The computing device 110 may also include other removable/non-removable, volatile/nonvolatile computer storage media products. By way of example only, FIG. 2 illustrates a non-removable non-volatile memory interface (hard disk interface) 140 that reads from and writes for example to non-removable, non-volatile magnetic media. FIG. 2 also illustrates a removable non-volatile memory interface 150 that, for example, is coupled to a magnetic disk drive 151 that reads from and writes to a removable, non-volatile magnetic disk 152, and/or is coupled to an optical disk drive 155 that reads from and writes to a removable, non-volatile optical disk 156, such as a CD ROM. Other removable/nonremovable, volatile/non-volatile computer storage media that can be used in the exemplary operating environment include, but are not limited to, magnetic tape cassettes, memory cards, flash memory cards, DVDs, digital video tape, solid state RAM, and solid state ROM. The hard disk drive 141 is typically connected to the system bus 121 through a non-removable memory interface, such as the interface 140, and magnetic disk drive 151 and optical disk drive 155 are typically connected to the system bus 121 by a removable non-volatile memory interface, such as interface 150.

The drives and their associated computer storage media discussed above and illustrated in FIG. 2 provide storage of computer-readable instructions, data structures, program modules, and other data for the computing device 110. In FIG. 2, for example, hard disk drive 141 is illustrated as storing an operating system 144, application programs 145, other program modules 146, and program data 147. Note that these components can either be the same as or different from the operating system 134, application programs 135, other program modules 136, and program data 137. The operating system 144, application programs 145, other program modules 146, and program data 147 are given different numbers here to illustrate that, at a minimum, they are different copies. A user may enter commands and information into the computing device 110 through input devices such as a microphone 163, keyboard 162, and pointing device 161, commonly referred to as a mouse, trackball, or touch pad. Other input devices (not shown) may include a joystick, game pad, satellite dish, and scanner. These and other input devices are often connected to the processing unit 120 through a user input interface 160 that is coupled to the system bus, but may be connected by other interface and bus structures, such as a parallel port, game port, or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 195.

The computing system environment 100 may operate in a networked environment using logical connections to one or more remote computers, such as a remote computer 180. The remote computer 180 may be a personal computer, a server, a router, a network PC, a peer device, or other common network node, and typically includes many or all of the elements described above relative to the computing device 110, although only a memory storage device 181 has been illustrated in FIG. 2. The network logical connections depicted in FIG. 2 include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing system environment 100 is connected to the network 171 through a network interface, such as the network interface 170, the modem 172, and/or the wireless interface 193. The network may include a LAN network environment, and/or a WAN network environment, such as the Internet. In a networked environment, program modules depicted relative to the computing device 110, or portions thereof, may be stored in a remote memory storage device. By way of example, and not limitation, FIG. 2 illustrates remote application programs 185 as residing on computer storage medium 181. It will be appreciated that the network connections shown are exemplary and other means of establishing communications link between the computers may be used.

Figure 3:
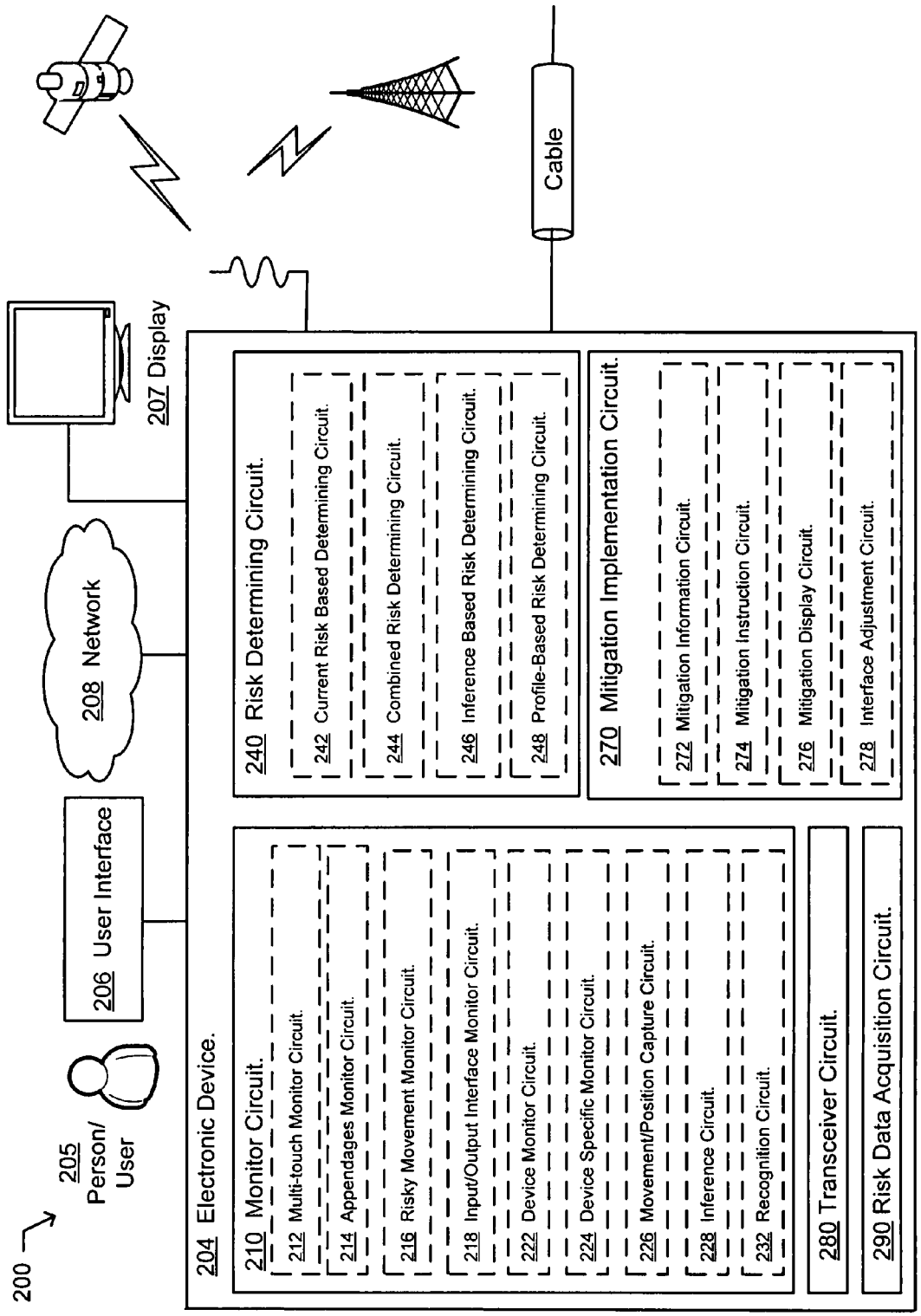
FIG. 3 illustrates an exemplary system in which embodiments may be implemented.

FIG. 3 illustrates an example system 200 in which embodiments may be implemented. The example system includes an electronic device 204, a user interface 206, and a display 207. The user interface may be physically incorporated with the electronic device, or may be physically separate from the electronic device and electronically coupled with the device. The display may be physically incorporated with the electronic device, or may be physically separate from the electronic device and electronically coupled with the device. The system may include a wired or wireless access to digital content, such as to the network 208. In an alternative embodiment, the electronic device may be coupled to the network 208 via a wireless link, a satellite link, and/or a wired link.

In an embodiment, the electronic device 204 includes a monitor circuit 210, a risk determining circuit 230, and a mitigation implementation circuit 270. In some embodiments, one or more of the monitor circuit, the risk determining circuit, and/or the mitigation implementation circuit may be structurally distinct from the remaining circuits. In an embodiment, the electronic device or a portion of the electronic device may be implemented in whole or in part using the thin computing device 20 described in conjunction with FIG. 1, and/or the computing device 110 described in conjunction with FIG. 2. In another embodiment, the electronic device or a portion of the electronic device may be implemented using Application Specific Integrated Circuits (ASICs), Field Programmable Gate Arrays (FPGAs), digital signal processors (DSPs), or other integrated formats. In a further embodiment, one or more of the circuits and/or the machine may be implemented in hardware, software, and/or firmware. A person 205 may interact with the electronic device 204 via a user interface 206.

The electronic device 204 may include at least one additional circuit. The at least one additional circuit may include a transceiver circuit 280, or a risk data acquisition circuit 290. In addition, the electronic device may include a processor (not illustrated), such as the processing unit 21 described in conjunction with FIG. 1, and/or the processor 120 described in conjunction with FIG. 2. In further addition, the electronic device may include a computer storage media (not illustrated). In an embodiment, the first wireless communication electronic device may include a mobile electronic device.

In an embodiment, the monitor circuit 210 may include at least one additional circuit. The at least one additional circuit may include at least one of a multi-touch monitor circuit 212, an appendages monitor circuit 214, a risky movement monitor circuit 216, an input/output interface monitor circuit 218, a device monitor circuit 222, a device specific monitor circuit 224, a movement/position capture circuit 226, an inference circuit 228, or a recognition circuit 232.

In another embodiment, the risk determining circuit 240 may include at least one additional circuit. The at least one additional circuit may include at least one of a current risk based determining circuit 242, a combined current and historical risk based determining circuit 244, an inference based risk determining circuit 246, or a profile based risk determining circuit 248.

In a further embodiment, the mitigation implementation circuit 270 may include at least one additional circuit. The at least one additional circuit may include at least one of a mitigation information circuit 272, a mitigation instruction circuit 274, a mitigation display circuit 276, or an interface adjustment circuit 278.

FIG. 4 illustrates an example of an operational flow 400 implemented in an environment that includes a person interacting with an electronic device via a user interface. FIG. 4 and several following figures may include various examples of operational flows, discussions, and explanations with respect to the above-described system 200 of FIG. 3, and/or with respect to other examples and contexts. However, it should be understood that the operational flows may be executed in a number of other environments and contexts, and/or in modified versions of FIG. 3. Also, although the various operational flows are illustrated in a sequence(s), it should be understood that the various operations may be performed in other orders than those which are illustrated, and/or may be performed concurrently.

After a start operation implemented in the environment that includes a person interacting with an electronic device via a user interface, the operational flow 400 includes an observation operation 410. The observation operation monitors at least one of a movement or a position of an appendage of the person with respect to the user interface of the device. The observation operation may be implemented using the monitoring circuit 210 of FIG. 3. In an embodiment, an appendage includes a portion of the person's body involved in interacting with the electronic device. The portion of the person's body involved may include their hands and fingers if keyboarding, or one or more fingers if they are working with a touch screen, an Apple iPhone™, or Microsoft's Surface™.

An ascertainment operation 440 determines if the monitored movement or position of the appendage of the person is indicative of a risk of a repetitive injury to the person. In an embodiment, a repetitive injury may include a repetitive strain injury—commonly known as RSI. A repetitive injury may include at least one of carpal tunnel syndrome, or muscle and tendon disorder. A repetitive injury may include damage to tendons, nerves, and other soft tissues that is caused by the repeated performance of a limited number of physical movements, and may be characterized by numbness, pain, and a wasting and weakening of muscles. The ascertainment operation may be implemented using the risk determining circuit 240 of FIG. 3. A mitigation operation 470 implements an action facilitating a reduction of the determined indicated risk of a repetitive injury to the person. The mitigation operation may be implemented using the mitigation implementation circuit 270 of FIG. 3. The operational flow 400 then proceeds to an end operation.

The operational flow 400 may include at least one additional operation. The at least one additional operation may include a risk data acquisition operation 490. The risk data acquisition operation acquires data indicative of at least one of a movement or a position of an appendage of the person with respect to the user interface of the device. The risk data acquisition operation may be implemented using the risk data acquisition circuit 290 of FIG. 3.

FIG. 5 illustrates an alternative embodiment of the operational flow 400 of FIG. 4. The observation operation 410 may include at least one additional operation. The at least one additional operation may include an operation 412, an operation 414, an operation 416, an operation 418, or an operation 422. The operation 412 monitors at least one of a multi-touch movement of an appendage of the person with respect to the user interface of the device. In an embodiment, a multi-touch movement may include a series of individual finger movements. In another embodiment, a multi-touch movement may include at least two fingers forming a combined movement, such as spreading two finger tips apart on a surface. The operation 412 may be implemented using the multi-touch monitor circuit 212. The operation 414 monitors at least one of a movement or a position of at least one of a head, arm, arms, wrist, hand, wrists, finger, fingers, finger speed, finger position with respect to keyboard, finger spreading, or finger striking force of the person with respect to the user interface of the device. The operation 414 may be implemented using the appendages monitor circuit 214. The operation 416 monitors for at least one of a class of risky repetitive movements or positions of the person with respect to the user interface of the device. The operation 416 may be implemented using the risky movements monitor circuit 216. The operation 418 monitors at least one of a movement or a position of an appendage of the person with respect to a user input interface, and/or a user output interface of the device. The operation 418 may be implemented using the input/output interface monitor circuit 218. The operation 422 monitors at least one of a movement or a position of an appendage of the person with respect to at least one of a keyboard, mouse, display screen, touch display screen, touch display surface, or interactive display surface of the electronic device. The operation 422 may be implemented using the device monitor circuit 222.

Figure 6:
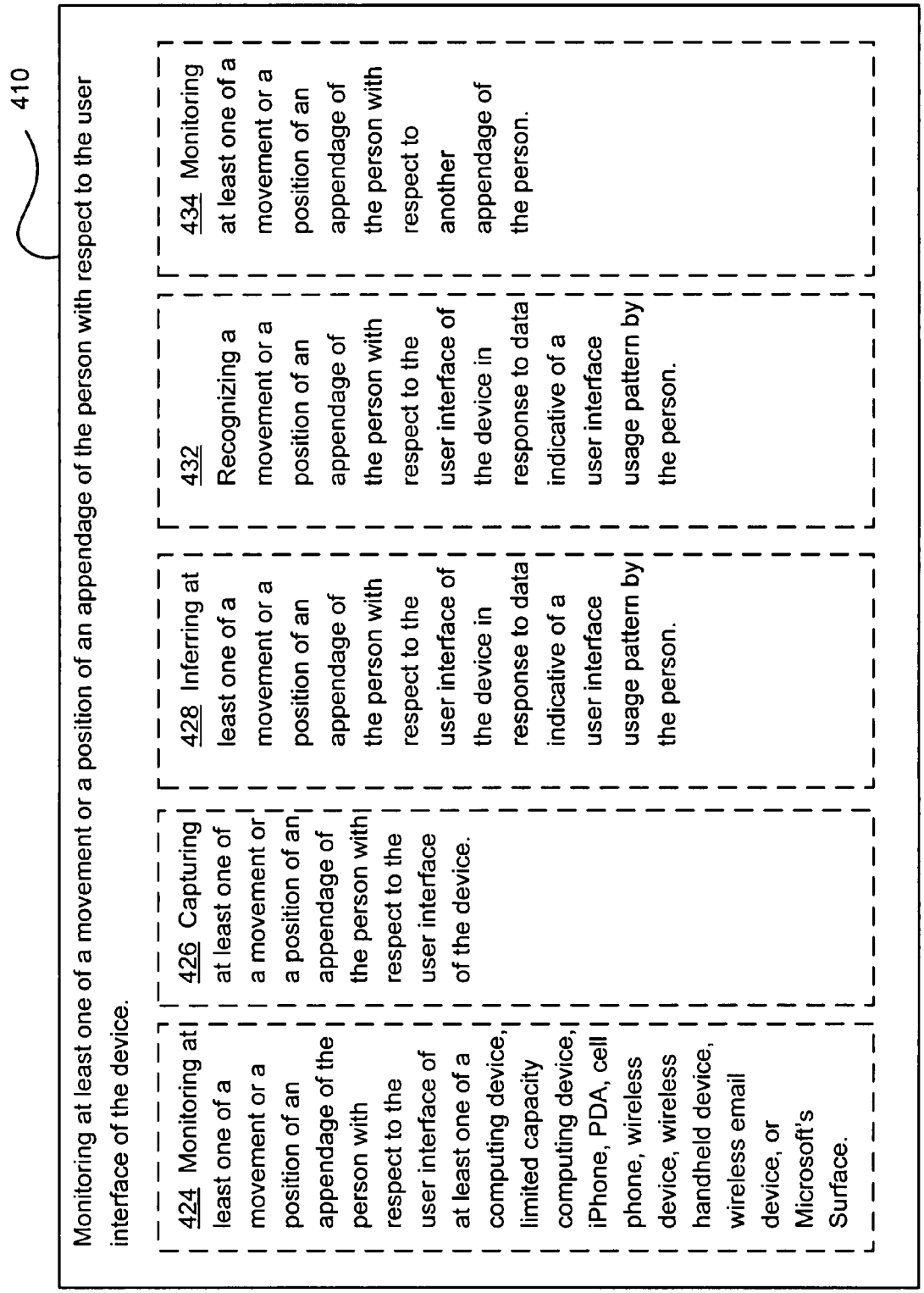
FIG. 6 illustrates another alternative embodiment of the operational flow of FIG. 4.

FIG. 6 illustrates another alternative embodiment of the operational flow 400 of FIG. 4. The observation operation 410 may include at least one additional operation. The at least one additional operation may include an operation 424, an operation 426, an operation 428, an operation 432, an operation 434, or an operation 436. The operation 424 monitors at least one of a movement or a position of an appendage of the person with respect to the user interface of at least one of a computing device, limited capacity computing device, iPhone, PDA, cell phone, wireless device, wireless handheld device, wireless email device, or Microsoft's Surface. The operation 424 may be implemented using the device specific monitor circuit 224. The operation 426 captures at least one of a movement or a position of an appendage of the person with respect to the user interface of the device. For example, one or more of the cameras of Microsoft's Surface may capture a movement or a position of an appendage of the person with respect to the surface of the Surface device. The operation 426 may be implemented using the movement/position capture circuit 226. The operation 428 infers at least one of a movement or a position of an appendage of the person with respect to the user interface of the device in response to data indicative of a user interface usage pattern by the person. The operation 428 may be implemented using the inference circuit 228. The operation 432 recognizes a movement or a position of an appendage of the person with respect to the user interface of the device in response to data indicative of a user interface usage pattern by the person. The operation 432 may be implemented using the recognition circuit 232. The operation 434 monitors at least one of a movement or a position of an appendage of the person with respect to another appendage of the person. In an alternative embodiment, the operation 434 monitors at least one of a movement or a position of an appendage of the person with respect to another appendage of the person and further with respect to the user interface. The operation 436 (not shown) monitors at least one of a current movement or a current position of an appendage of the person with respect to the user interface of the device.

FIG. 7 illustrates a further alternative embodiment of the operational flow 400 of FIG. 4. The ascertainment operation 440 may include at least one additional operation. The at least one additional operation may include an operation 442, an operation 444, an operation 446, or an operation 448. The operation 442 determines if the monitored at least one of a current movement or a current position of the appendage of the person indicates a risk of a repetitive injury to the person. The operation 442 may be implemented using the current risk based determining circuit 343. The operation 444 determines if a combination of the monitored at least one of a current movement or a current position of the appendage of the person and a monitored at least one of a past movement or a past position of the appendage of the person indicates a risk of a repetitive injury to the person. The operation 444 may be implemented using the combined risk determining circuit 244. The operation 446 infers a usage pattern in response to the monitored at least one of a movement or a position of the appendage of the person and determines if the inferred usage pattern indicates a risk of a repetitive injury to the person. The operation 446 may be implemented using the inference based risk determining circuit 246. The operation 448 determines if a combination of the monitored at least one of a movement or position of the appendage of the person and an inputted repetitive injury profile of the person is indicative of a risk to the person of a current repetitive injury. The operation 448 may be implemented using the profile-based risk determining circuit 248.

FIG. 8 illustrates an alternative embodiment of the operational flow 400 of FIG. 4. The mitigation operation 470 may include at least one additional operation. The at least one additional operation may include an operation 472, an operation 474, an operation 476, or an operation 478. The operation 472 displays using the electronic device a warning facilitating a reduction of the indicated risk of a repetitive injury to the person. The operation 472 may be implemented using the mitigation information circuit 272 of FIG. 3. The operation 474 displays using an aspect of the electronic device a human understandable instruction facilitating a reduction of the indicated risk of a repetitive injury to the person. For example, the human understandable instruction may include one or more hints how to reduce the indicated risk of repetitive injury. By way of further example, the human understandable instruction may include a pointer arrow indicating where fingers should be placed for reduced risk, and/or a demonstration or illustration of an alternative positioning. For example, as a person spreads their fingers wider and wider as they expands a photo on an iPhone, the system detects that the fingers are in an awkward and potentially unhealthy conformation and (possibly because he has done similar or related things a lot recently with his hands) highlights areas on the screen where he could more safely/comfortably put his fingers and still expand the photo. The operation 474 may be implemented using the mitigation instruction circuit 274. The operation 476 displays, using an aspect of the electronic device, a human understandable information facilitating a reduction of the indicated risk of a repetitive injury to the person. For example, a direct presentation of combined warning and alternatives, such as showing good/bad screen regions for placement of a finger that will accomplish the same task the user is attempting. The operation 476 may be implemented using the mitigation display circuit 276.

The operation 478 modifies an aspect of the user interface of the device facilitating a reduction of the indicated risk to the person of a repetitive injury. In an embodiment, the modifying an aspect of the user interface may include adjusting a parameter of the user interface. In another embodiment, the modifying an aspect of the user interface includes modifying a parameter of the user interface. In addition to modifying an aspect of the user interface to facilitate a reduction of the indicated risk, the modifying may include a modifying an aspect of the user interface to improve the effectiveness human-user interface interaction. Further, in addition to modifying an aspect of the user interface to facilitate a reduction of the indicated risk, the modifying may include a modifying an aspect of the user interface to improve the health of the person with respect to using the electronic device. For example, facilitation of a reduction of the indicated risk may be achieved by reducing/enhancing the effectiveness of certain less display screen areas so that the person gravitates towards or away from safe or unsafe areas as they try to get a task done. Continuing the above example, the display areas that cause the person to spread their fingers too widely could become less effective in expanding the image, while safer areas become more effective. This process could be combined with the above instructions or information such that the display could provide hints (e.g., a small arrow) pointing in the direction that the user should shift a finger for more effective and healthy positioning. The operation 478 may be implemented using the interface adjustment circuit 278.

Figure 9:
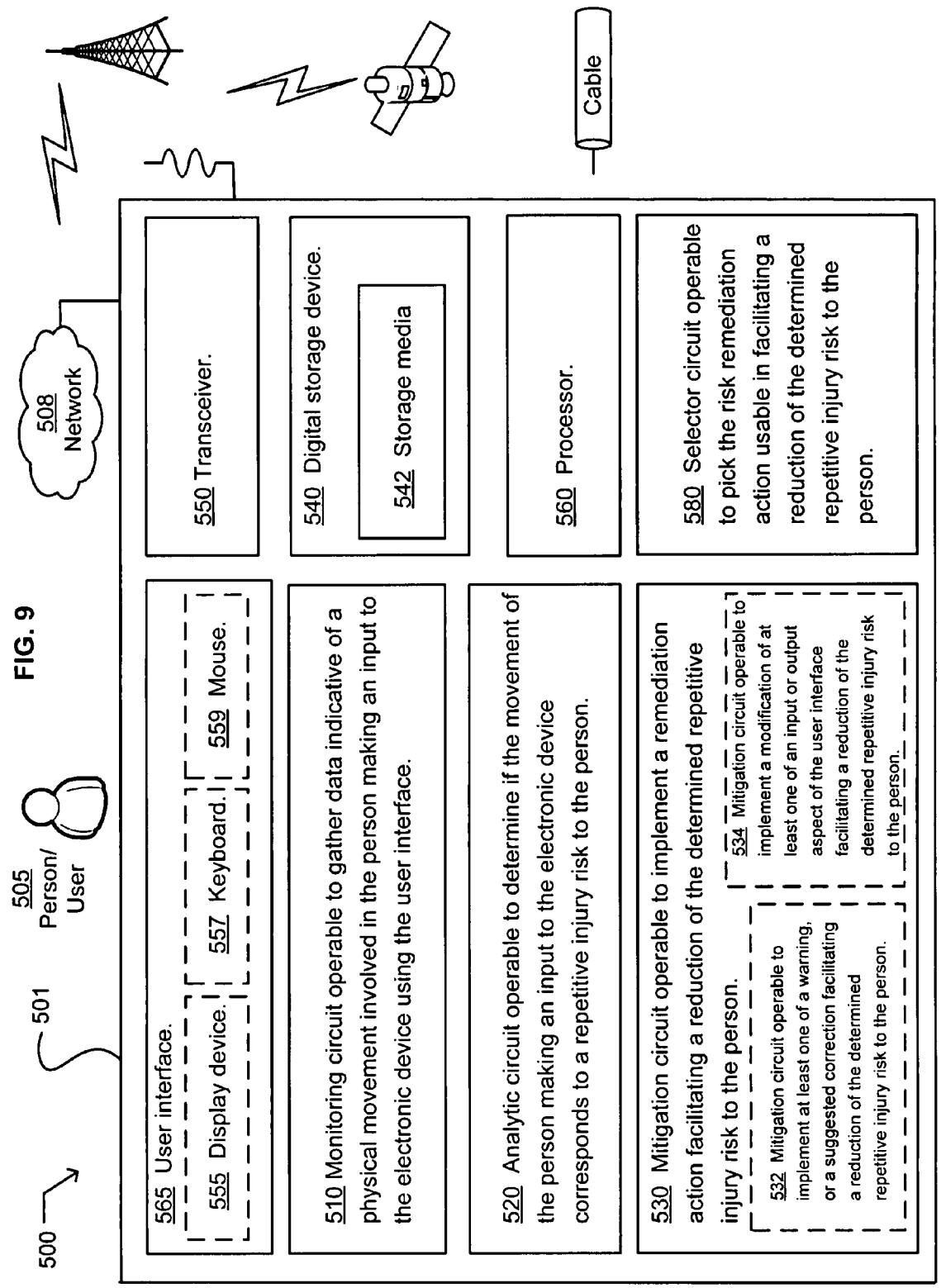
FIG. 9 illustrates an example environment in which embodiments may be implemented.

FIG. 9 illustrates an example environment 500 in which embodiments may be implemented. The environment includes an electronic device 501. The electronic device may be coupled to the network 508 via a wireless link, a satellite link, and/or a wired link. The electronic device includes a monitoring circuit 510, an analytic circuit 520, a mitigation circuit 530, and a user interface 565. In some embodiments, one or more of the monitoring circuit, the analytic circuit, and/or the mitigation circuit may be structurally distinct from the remaining circuits. In an embodiment, the electronic device or a portion of the electronic device may be implemented in whole or in part using the thin computing device 20 described in conjunction with FIG. 1, and/or the computing device 10 described in conjunction with FIG. 2. In another embodiment, the electronic device or a portion of the electronic device may be implemented using Application Specific Integrated Circuits (ASICs), Field Programmable Gate Arrays (FPGAs), digital signal processors (DSPs), or other integrated formats. In a further embodiment, one or more of the circuits and/or the machine may be implemented in hardware, software, and/or firmware. In addition, the electronic device may include at least one of a digital storage device 540, a transceiver 550, or a processor 560. The user interface may include at least one of a display device 555, a keyboard 557, a mouse 559, or a surface (not shown). A person 505 may interact with the electronic device 501 via a user interface 565.

The user interface 565 includes a user interface operable to at least one of receive input from a person 505 or provide an output to the person. The monitoring circuit 510 includes a monitoring circuit operable to gather data indicative of a physical movement involved in the person making an input to the electronic device using the user interface. The analytic circuit 520 includes an analytic circuit operable to determine if the movement of the person making an input to the electronic device corresponds to a repetitive injury risk to the person. The mitigation circuit 530 includes a mitigation circuit operable to implement a remediation action facilitating a reduction of the determined repetitive injury risk to the person. In an alternative embodiment, the mitigation circuit further includes a mitigation circuit 532 operable to implement at least one of a warning, or a suggested correction facilitating a reduction of the determined repetitive injury risk to the person. In a further embodiment, the mitigation circuit further includes a mitigation circuit 534 operable to implement a modification of at least one of an input or output aspect of the user interface facilitating a reduction of the determined repetitive injury risk to the person.

In another alternative embodiment, the electronic device 501 further includes a selector circuit 580 operable to pick the risk remediation action usable in facilitating a reduction of the determined repetitive injury risk to the person.

FIG. 10 illustrates an example computer program product 600. The computer program product includes a computer-readable signal-bearing medium 610 bearing program instructions 620. The program instructions are operable to perform a process in a computing device having a user interface operable to interact with a person. The process includes monitoring at least one of a movement or a position of an appendage of the person with respect to the user interface of the device. The process also includes determining if the monitored movement or position of the appendage of the person is indicative of a risk of a repetitive injury to the person. The process further includes implementing action facilitating a reduction of the determined indicated risk of a repetitive injury to the person. In an embodiment, the computer-readable signal-bearing medium includes a computer storage medium 612. In another embodiment, the computer-readable signal-bearing medium includes a communication medium 614.

FIG. 11 illustrates an example system 700. The system includes an electronic device 705 having a user interface operable to interact with a person. The electronic device includes means 710 for monitoring at least one of a movement or a position of an appendage of the person with respect to the user interface of the device. The electronic device also includes means 720 for determining if the monitored movement or position of the appendage of the person is indicative of a risk of a repetitive injury to the person. The electronic device further includes means 730 for implementing an action facilitating a reduction of the determined indicated risk of a repetitive injury to the person The foregoing detailed description has set forth various embodiments of the systems, apparatus, devices, computer program products, and/or processes using block diagrams, flow diagrams, operation diagrams, flowcharts, illustrations, and/or examples. A particular block diagram, operation diagram, flowchart, illustration, environment, and/or example should not be interpreted as having any dependency or requirement relating to any one or combination of components illustrated therein. For example, in certain instances, one or more elements of an environment may be deemed not necessary and omitted. In other instances, one or more other elements may be deemed necessary and added.

Insofar as such block diagrams, operation diagrams, flowcharts, illustrations, and/or examples contain one or more functions and/or operations, it will be understood that each function and/or operation within such block diagrams, operation diagrams, flowcharts, illustrations, or examples can be implemented, individually and/or collectively, by a wide range of hardware, software, firmware, or virtually any combination thereof unless otherwise indicated. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware. Those skilled in the art will recognize that optical aspects of implementations will typically employ optically-oriented hardware, software, and or firmware.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method to migrate repetitive strain comprising:
providing an electronic device including a touch screen display and a camera;
interacting with the electronic device by touching a user interface displayed on the touch screen display of the electronic device with at least a portion of a person's appendage;
detecting with the camera at least one of the position or movement of the person's appendage as at least the portion the appendage touches the user interface;
capturing and saving with the camera an image of the appendage touching the user interface;
recording changes with the touch screen display in an electric charge flowing via the display in response to a portion of the appendage touching the displayed user interface;
monitoring with the electronic device at least one of a position or a movement of the person's appendage as at least the portion the appendage touches the user interface to determine at least one of a movement or a position of the appendage;

determining with the electronic device if the monitored at least one of the movement or the position of the person's appendage as at least the portion of the person's appendage repetitively touches the user interface is indicative of a risk of a repetitive injury to the person;

identifying with the electronic device a risk remediation action to reduce the determined indicated risk of a repetitive injury to the person; and implementing with the electronic device the risk remediation action by modifying aspects of the user interface to indicate to the person to change at least one of the position or movement of the appendage as the portion of the person's appendage touches the user interface to reduce the determined indicated risk of a repetitive injury to the person.

2. The method of claim 1, wherein the monitoring at least one of a movement or a position of an appendage as at least the portion the appendage touches the user interface further includes:

monitoring at least one of a multi-touch movement of an appendage of the person as at least the portion the appendage touches the user interface.

3. The method of claim 1, wherein the monitoring at least one of a movement or a position of an appendage as at least the portion the appendage touches the user interface further includes:

monitoring at least one of a movement or a position of at least one of a head, arm, arms, wrist, hand, wrists, finger, fingers, finger speed, finger position with respect to keyboard, finger spreading, or finger striking force of the person as at least the portion the appendage touches the user interface.

4. The method of claim 1, wherein the monitoring with the electronic device at least one of a movement or a position of the person's appendage as at least the portion of the appendage touches the user interface of the device further includes:

monitoring for at least one of a class of risky repetitive movements or positions of the person's appendage in response to at least the portion the appendage touching a surface of the user interface of the device.

5. The method of claim 1, wherein the monitoring at least one of a movement or a position of an appendage of the person as at least the portion the appendage touches the user interface further includes:

monitoring at least one of a movement or a position of an appendage of the person as at least the portion the appendage touches a user input interface, and/or a user output interface.

6. The method of claim 1, wherein the monitoring at least one of a movement or a position of an appendage of the person as at least the portion the appendage touches the user interface further includes:

monitoring at least one of a movement or a position of an appendage of the person as at least the portion the appendage touches at least one of a keyboard, mouse, display screen, touch display screen, touch display surface, or interactive display surface of the electronic device.

7. The method of claim 1, wherein the monitoring with the electronic device at least one of a movement or a position of the person's appendage as at least the portion the appendage touches the user interface of the device further includes:

monitoring at least one of a movement or a position of an appendage of the person's appendage in response to at least the portion the appendage touching the user interface of at least one of a computing device, limited capacity computing device, internet Phone, PDA, cell phone, wireless device, wireless handheld device, or wireless email device.

8. The method of claim 1, wherein the monitoring at least one of a movement or a position of an appendage of the person as at least the portion the appendage touches the user interface further includes:

capturing at least one of a movement or a position of an appendage of the person as at least the portion the appendage touches the user interface.

9. The method of claim 1, wherein the monitoring at least one of a movement or a position of an appendage of the person as at least the portion the appendage touches the user interface further includes:

inferring at least one of a movement or a position of an appendage of the person as at least the portion the appendage touches the user interface in response to data indicative of a user interface usage pattern by the person.

10. The method of claim 1, wherein the monitoring at least one of a movement or a position of an appendage of the person as at least the portion the appendage touches the user interface further includes:

recognizing a movement or a position of an appendage of the person as at least the portion the appendage touches the user interface in response to data indicative of a user interface usage pattern by the person.

11. The method of claim 1, wherein the monitoring at least one of a movement or a position of an appendage of the person as at least the portion the appendage touches the user interface further includes:

monitoring at least one of a movement or a position of an appendage of the person as at least the portion the appendage touches another appendage of the person.

12. The method of claim 1, wherein the determining if at least one of the monitored movement or position of the appendage of the person as at least the portion of the person's appendage repetitively touches the user interface is indicative of a risk of a repetitive injury to the person further includes:

determining if at least one of the monitored current movement or current position of the appendage of the person as at least the portion of the person's appendage repetitively touches the user interface is indicative of a risk of a repetitive injury to the person.

13. The method of claim 1, wherein the determining if at least one of the monitored movement or position of the appendage of the person as at least the portion of the person's appendage repetitively touches the user interface is indicative of a risk of a repetitive injury to the person further includes:

determining if a combination of at least one of the monitored current movement or current position of the appendage of the person and a monitored a past movement or a past position of the appendage of the person as at least the portion of the person's appendage repetitively touches the user interface indicates a risk of a repetitive injury to the person.

14. The method of claim 1, wherein the determining if at least one of the monitored movement or position of the appendage of the person as at least the portion of the person's appendage repetitively touches the user interface is indicative of a risk of a repetitive injury to the person further includes:

inferring a usage pattern in response to at least one of the monitored movement or position of the appendage of the person and determining if the inferred usage pattern as at least the portion of the person's appendage repetitively touches the user interface indicates a risk of a repetitive injury to the person.

15. The method of claim 1, wherein the determining if the monitored at least one of the movement or the position of the person's appendage as at least the portion of the person's appendage repetitively touches the user interface is indicative of a risk of a repetitive injury to the person further includes:
   determining if a combination of the monitored at least one of the movement or the position of the person's appendage in response to at least the portion of the person's appendage repetitively touches the user interface and an inputted repetitive injury profile of the person indicates a risk to the person of a current repetitive injury.

16. The method of claim 1, wherein the implementing the risk remediation action by modifying aspects of the user interface includes:
   displaying using the electronic device a warning facilitating a reduction of the indicated risk of a repetitive injury to the person.

17. The method of claim 1, wherein monitoring with the electronic device at least one of the position or the movement of the person's appendage as at least the portion the appendage touches the user interface of the device to determine at least one of the movement or the position of the appendage comprises:
   monitoring using the saved image from the camera to detect movement or a position of an appendage of the person's appendage in response to at least the portion the appendage touching the user interface of the device.

18. An electronic device comprising:
   a camera to detect at least one of a position or a movement of a person's appendage as at least a portion the appendage touches a user interface displayed on a touch screen display, the camera operable to capture and save an image of the appendage with respect to the user interface, the touch screen display operable to record change in an electric charge flowing via the touch screen display in response to the portion of the appendage touching the user interface; and
   a non-transitory medium including at least one or more instructions executed by a processor for:
      receiving an input from or providing an output to the person via the user interface;
      gathering data indicative of at least one of the physical movement or position of the appendage of the person in response to at least the portion of the appendage touching the user interface to enable the person to make an input to the electronic device via the user interface;
      determining if the movement or position of the appendage of the person in response to at least a portion of the appendage touching the user interface to make an input to the electronic device corresponds to a repetitive injury risk to the person;
      picking a risk remediation action to facilitate a reduction of the determined repetitive injury risk to the person; and
      implementing the risk remediation action by modifying aspects of the user interface to indicate to the person to change at least one of a position or movement of the at least the portion of the person's appendage touching the user interface to facilitate a reduction of the determined repetitive injury risk to the person.

19. The electronic device of claim 18, wherein implementing the risk remediation action by modifying aspects of the user interface to indicate to the person to change at least one of a position or movement of the at least the portion of the person's appendage touching the user interface to facilitate the reduction of the determined repetitive injury risk to the person further includes:
   implemementing at least one of a warning, or a suggested correction by modifying aspects of the user interface to indicate to the person to change at least one of a position or movement of the at least the portion of the person's appendage touching the user interface to facilitate the reduction of the determined repetitive injury risk to the person.

20. The electronic device of claim 18, wherein the one or more instructions executed by the processor for implementing the risk remediation action to facilitate a reduction of the determined repetitive injury risk to the person further includes:
   one or more instructions executed by the processor for implementing a modification of at least one of an input or output aspect of the user interface to facilitate a reduction of the determined repetitive injury risk to the person.

21. The electronic device of claim 18, wherein the one or more instructions executed by the processor for implementing a remediation action to facilitate a reduction of the determined repetitive injury risk to the person further includes:
   one or more instructions executed by the processor for implementing a modification of an aspect of the user interface to improve effectiveness of interaction between the person and the user interface.

22. A computer product comprising:
   (a) a processor to execute program instructions to perform a process in a computing device having a touch screen display with a user interface operable to interact with a person, the computing device coupled with a camera to detect at least one of a position or a movement of a person's appendage as at least a portion the appendage touches the user interface, the camera operable to capture and save an image of the appendage with respect to the user interface, the touch screen display operable to record change in an electric charge flowing via the touch screen display in response to the portion of the appendage touching the user interface, the process comprising:
      monitoring via the camera or the touch screen display at least one of movement or position of an appendage of the person in response to at least a portion of the appendage touching the user interface of the computing device;
      determining if the monitored movement of the appendage of the person is indicative of a risk of a repetitive injury to the person;
      selecting a risk remediation action configured for facilitating a reduction of the determined indicated risk of a repetitive injury to the person; and
      implementing the risk remediation action by suggesting via the user interface to the person at least one of a corrected movement or position of the appendage as at least a portion of the appendage touches the user interface to facilitate a reduction of the determined indicated risk of a repetitive injury to the person; and
   (b) a non-transitory computer-readable medium bearing the program instructions.

23. An electronic device comprising:
an input device and an output device with a touch screen display having a user interface operable to interact with a person, the touch screen display to record changes in an electric charge flowing via the touch screen display in response to a portion of an appendage of the person touching the touch screen display; and
a non-transitory medium including at least one or more instructions executed by a processor to:
monitor a multi-touch gesture movement of the appendage as the person touches the touch screen display's user interface of the input and output device;
determine if the monitored multi-touch gesture movement of the appendage as the person touches the touch screen display's user interface of the input and output device is indicative of a risk of a repetitive injury to the person;
pick a risk remediation action usable to facilitate a reduction of the determined repetitive injury risk to the person; and
implement the risk remediation action by demonstration or illustration of alternate multi-touch gesture movements of the appendage via the touch screen display's user interface to facilitate a reduction of the determined indicated risk of a repetitive injury to the person.

24. The electronic device of claim 18, wherein one or more instructions executed by the processor for determining if the movement or position of the appendage of the person in response to at least a portion of the appendage touching the user interface to make an input to the electronic device corresponds to a repetitive injury risk to the person further includes:
one or more instructions executed by the processor for determining if the movement or position of the appendage of the person in response to at least a portion of the appendage touching the user interface to make an input to the electronic device is a multi-touch gesture movement.

25. The method as recited in claim 1, wherein at least the portion of the person's appendage includes hands and fingers.

26. The method as recited in claim 1, wherein implementing with the electronic device the risk remediation action by modifying aspects of the user interface to indicate to the person to change at least one of the position or movement of the appendage as the portion of the person's appendage touches the user interface to reduce the determined indicated risk of a repetitive injury to the person includes:
implementing with the electronic device the risk remediation action by modifying parameters displayed on the user interface to indicate to the person to change at least one of the position or movement of the appendage as the portion of the person's appendage touches the user interface to reduce the determined indicated risk of a repetitive injury to the person.

* * * * *